(12) United States Patent
Hirakawa et al.

(10) Patent No.: US 12,308,100 B2
(45) Date of Patent: May 20, 2025

(54) MEDICAL CARE SUPPORT DEVICE (71) Applicant: FUJIFILM Corporation, Tokyo (JP)

(72) Inventors: Tsuyoshi Hirakawa, Tokyo (JP); Keiji Tsubota, Tokyo (JP); Misaki Kawahara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 61 days.

(21) Appl. No.: 17/677,946

(22) Filed: Feb. 22, 2022

(65) Prior Publication Data

US 2022/0180989 A1 Jun. 9, 2022

Related U.S. Application Data

(63) Continuation of application No. PCT/JP2020/026374, filed on Jul. 6, 2020.

(30) Foreign Application Priority Data

Sep. 27, 2019 (JP) ................................ 2019-177807

(51) Int. Cl.
*G16H 15/00* (2018.01)
*G06F 40/103* (2020.01)
*G16H 10/60* (2018.01)

(52) U.S. Cl.
CPC ........... *G16H 15/00* (2018.01); *G06F 40/103* (2020.01); *G16H 10/60* (2018.01)

(58) Field of Classification Search
CPC .............................. G16H 10/60; G06F 40/103
See application file for complete search history.

(56) References Cited

U.S. PATENT DOCUMENTS 8,625,867 B2 1/2014 Moriya
10,169,453 B2 * 1/2019 Luo ....................... G06F 16/345
(Continued)

FOREIGN PATENT DOCUMENTS

JP 2001249998 9/2001
JP 2002207823 7/2002
(Continued)

OTHER PUBLICATIONS

"International Search Report (Form PCT/ISA/210) of PCT/JP2020/026374," mailed on Sep. 29, 2020, with English translation thereof, pp. 1-5.
(Continued)

*Primary Examiner* — William L Bashore
*Assistant Examiner* — Gregory A Distefano
(74) *Attorney, Agent, or Firm* — JCIPRNET (57) ABSTRACT

A medical care support device includes: a medical care document generation unit that generates a discharge summary, which is a medical care document in which extracted data extracted from medical care data related to medical care of a patient is laid out in a predetermined format; and a display screen generation unit that generates a medical care document display screen, which is a display screen having a first display area for displaying the discharge summary and a second display area for displaying original data which is medical care data of an extraction source of the extracted data. The display screen generation unit displays a correspondence between the extracted data and the original data in an identifiable manner on the medical care document display screen.

17 Claims, 7 Drawing Sheets

(56) References Cited

U.S. PATENT DOCUMENTS

| | | | |
|---|---|---|---|
| 10,909,215 B2 | 2/2021 | Wall et al. | |
| 11,036,352 B2 | 6/2021 | Yamane et al. | |
| 2002/0111932 A1* | 8/2002 | Roberge | G16H 15/00 |
| 2004/0186746 A1* | 9/2004 | Angst | G16H 10/65 |
| | | | 705/3 |
| 2005/0075905 A1* | 4/2005 | Bennett | G16H 15/00 |
| | | | 705/2 |
| 2007/0061165 A1* | 3/2007 | Ash | G16H 70/20 |
| | | | 600/300 |
| 2007/0260126 A1* | 11/2007 | Haumann | G16Z 99/00 |
| | | | 600/300 |
| 2009/0076792 A1* | 3/2009 | Lawson-Tancred | G06F 40/106 |
| | | | 704/2 |
| 2014/0348396 A1* | 11/2014 | Laaser | G06V 30/40 |
| | | | 382/113 |
| 2020/0069259 A1* | 3/2020 | Kano | G16H 30/20 |
| 2020/0279651 A1 | 9/2020 | Nenoki et al. | |
| 2021/0151138 A1 | 5/2021 | Wall et al. | |

FOREIGN PATENT DOCUMENTS

| | | |
|---|---|---|
| JP | 2003196389 | 7/2003 |
| JP | 2006059063 | 3/2006 |
| JP | 2008233952 | 10/2008 |
| JP | 2011014007 | 1/2011 |
| JP | 2011083590 | 4/2011 |
| JP | 2013186649 | 9/2013 |
| JP | 2015069446 | 4/2015 |
| JP | 2017162037 | 9/2017 |
| JP | 2017189383 | 10/2017 |
| JP | 6456539 | 1/2019 |
| JP | 2019003230 | 1/2019 |
| JP | 2019502983 | 1/2019 |
| JP | 2019105921 | 6/2019 |
| JP | 2019179451 | 10/2019 |
| WO | 2018192841 | 10/2018 |
| WO | 2019102949 | 5/2019 |

OTHER PUBLICATIONS

"Written Opinion of the International Searching Authority (Form PCT/ISA/237)" of PCT/ JP2020/026374, mailed on Sep. 29, 2020, with English translation thereof, pp. 1-6.

"Office Action of Japan Counterpart Application", issued on Mar. 14, 2023, with English translation thereof, p. 1-p. 7.

"Notice of Reasons for Refusal of Japan Counterpart Application", issued on Jul. 9, 2024, with English translation thereof, p. 1-p. 8.

"Decision of Refusal of Japan Counterpart Application", issued on Dec. 10, 2024, with English translation thereof, p. 1-p. 8.

* cited by examiner

SUMMARY AT DISCHARGE
FMS GENERAL HOSPITAL
2/2

| SURGERY/TREATMENT NAME | K CODE | SURGERY DATE | SURGEON | ANESTHESIOLOGIST |
|---|---|---|---|---|
| GERM LAYER RESECTION | K514-2 | FEBRUARY 19, 2014 | DOCTOR TARO | TARO MASUDA |

| | |
|---|---|
| SURGICAL TREATMENT FINDINGS | A LATERAL THORACOTOMY WAS PERFORMED WITH A 12 cm SKIN INCISION. VENTILATION WAS TEMPORARILY STOPPED, AND A PARTIAL RESECTION OF THE LEFT LOWER LOBE WAS PERFORMED WITH AN AUTOMATIC ENDOSCOPIC SUTURE DEVICE. A 16 mm TUMOR WAS DIAGNOSED AS MODERATELY DIFFERENTIATED FLAT EPITHELIAL CARCINOMA, AND IT WAS PATHOLOGICALLY UNKNOWN WHETHER THE INITIAL LUNG CANCER WAS METASTASIS TO THE LUNG OR METACHRONOUS MULTIPLE LUNG CANCER. POSTOPERATIVE COURSE: TRANSIENT ATRIAL FIBRILLATION WAS OBSERVED, BUT IT IMPROVED IMMEDIATELY. SINCE THE POSSIBILITY OF RECURRENCE OF THE FIRST LUNG CANCER CANNOT BE RULED OUT, 5 COURSES OF carboplatin + gemcitabine WERE PERFORMED AS adjuvant chemotherapy. AFTER THAT, DURING FOLLOW-UP, LEFT PNEUMOTHORAX WAS COMPLICATED AND THE CONDITION WAS IMPROVED BY DRAINAGE. POSTOPERATIVE COURSE: TRANSIENT ATRIAL FIBRILLATION WAS OBSERVED, BUT IT IMPROVED IMMEDIATELY. SINCE THE POSSIBILITY OF RECURRENCE OF THE FIRST LUNG CANCER CANNOT BE RULED OUT, 5 COURSES OF carboplatin + gemcitabine WERE PERFORMED AS adjuvant chemotherapy. AFTER THAT, DURING FOLLOW-UP, LEFT PNEUMOTHORAX WAS COMPLICATED AND THE CONDITION WAS IMPROVED BY DRAINAGE. A 16 mm TUMOR WAS DIAGNOSED AS MODERATELY DIFFERENTIATED FLAT EPITHELIAL CARCINOMA, AND IT WAS PATHOLOGICALLY UNKNOWN WHETHER THE INITIAL LUNG CANCER WAS METASTASIS TO THE LUNG OR METACHRONOUS MULTIPLE LUNG CANCER.  |
| SURGICAL TREATMENT FINDINGS | NO (YES)    ORDERED RAPID PATHOLOGY "WELL-DIFFERENTIATED ADENOCARCINOMA" <br> STUMP (−) |
| STAGE CLASSIFICATION | PROGRESSION: Stage 1    TNM CLASSIFICATION: T1N0M0    T:1    N:1    M:1 <br> LOWER LEFT LOBE S9 WELL-DIFFERENTIATED ADENOCARCINOMA |
| PROGRESS LEVEL | ☐ INTRAEPITHELIAL   ☒ LOCALITY   ☐ AFFILIATED LYMPH NODE TRANSFER   ☐ INFILTRATION OF ADJACENT ORGANS   ☐ DISTANT METASTASIS   ☐ NOT CLEAR |
| PROGRESS AFTER HOSPITALIZATION | LEFT LOWER LOBECTOMY WAS PERFORMED ON THE 3RD DAY AFTER ADMISSION. FASTED ON 2 DAYS INCLUDING THE DAY OF SURGERY, AND PORRIDGE FOR 5 MINUTES FROM THE 3RD DAY. THE THORACIC CONTINUOUS SUCTION DRAIN WAS REMOVED ON THE 4TH DAY. <br><br> EHYDRA WAS REMOVED ON THE 6TH DAY. (PAIN MANAGEMENT WITH VOLTAREN) <br><br> SINCE THE PAIN WAS RELIEVED AFTER THE SURGERY, WALKING TRAINING IN THE WARD WAS STARTED ON THE 6TH DAY AFTER THE SURGERY. A SLIGHT BRUISE OCCURRED ON THE RIGHT OCCIPITAL REGION DURING THE SURGERY, SO WE REQUESTED THE INTERVENTION OF THE PRESSURE ULCER MANAGEMENT TEAM AND OBSERVED IT. HEALED ON THE 13TH DAY.  |
| REMARKS | THERE IS A REQUEST TO ISSUE A MEDICAL CERTIFICATE. |
| TREATMENT POLICY | DUE TO THE EXCISION OF THE TUMOR, THERE IS NO TENDENCY TO SUSPECT TUMOR SURVIVAL OR METASTASIS IN EITHER DIAGNOSTIC IMAGING OR BIOCHEMICAL EXAMINATION. IN THE FUTURE, WE WILL FOLLOW UP AFTER SURGERY AT OUR HOSPITAL. FOLLOW-UP WILL BE CONDUCTED AT THE REFERRAL HOSPITAL IN ABOUT 3 MONTHS. | PRESCRIPTION AT DISCHARGE | VOLTAREN 200 mg 3T <br> CODEINE PHOSPHATE 100 mg 3P <br> GENANIC 100 mg 3T |

CREATED DATE   MARCH 25, 2014     CREATOR   DOCTOR TARO     APPROVER ________

MEDICAL CARE SUPPORT DEVICE

CROSS-REFERENCE TO RELATED APPLICATIONS

This application is a Continuation of PCT International Application No. PCT/JP2020/026374 filed on Jul. 6, 2020, which claims priority under 35 U.S.C § 119(a) to Japanese Patent Application No. 2019-177807 filed on Sep. 27, 2019. Each of the above application(s) is hereby expressly incorporated by reference, in its entirety, into the present application.

BACKGROUND OF THE INVENTION

1. Field of the Invention

The present invention relates to a medical care support device.

2. Description of the Related Art

In the medical field, various types of medical care documents such as an inpatient medical care plan showing the medical care schedule of a patient scheduled to be hospitalized, a discharge summary that is a summary of medical care performed during hospitalization, and a medical care information provision document that also functions as a referral letter to another medical institution are generated. In order to generate these medical care documents, it is necessary to select various information obtained in the patient's medical care process, which requires a great deal of time and effort. Therefore, in JP2017-162037A below, it is possible to generate an electronic medical record by a simple operation such as selecting displayed examination data. Further, JP2017-162037A below also has a function of extracting patient information from past medical records and transcribing the information. In addition, JP2019-502983A below describes a configuration in which machine learning is used to generate a more complete consent document.

SUMMARY OF THE INVENTION

In order to reduce the time and effort of generating medical care documents, it is conceivable that the machine side selects (extracts) and lays out information, that is, automatically generates medical care documents. However, in this case, there is a problem that an extraction source of the extracted information is unclear. In a case where the extraction source of the information is unclear in this way, even though incorrect information is extracted, it may be overlooked. Further, in a case where the extraction source of the information is unclear, it is difficult to specify the extraction source, and it takes time and effort to collate with the correct information.

The present disclosure has been made in view of the above background, and an object thereof is to provide a medical care support device in which an extraction source of extracted information is clear even though the information used for a medical care document is automatically extracted.

According to an aspect of the present disclosure, there is provided a medical care support device comprising: a medical care document generation unit that generates a medical care document in which extracted data extracted from medical care data related to medical care of a patient is laid out in a predetermined format; and a display screen generation unit that generates a display screen having a first display area for displaying the medical care document and a second display area for displaying original data which is medical care data of an extraction source of the extracted data.

The display screen generation unit may display a correspondence between the extracted data and the original data in an identifiable manner on the display screen.

The display screen generation unit may highlight, in a case where any of the extracted data is selected in the first display area, the original data corresponding to the selected extracted data in the second display area.

The display screen may have a third display area for displaying, for each of the medical care data, a medical care period in which the medical care related to an acquisition of each piece of medical care data is performed in time series.

The display screen generation unit may display a correspondence between the extracted data and the medical care period in an identifiable manner on the display screen.

The display screen generation unit may highlight, in a case where any of the extracted data is selected in the first display area, the medical care period corresponding to the selected extracted data in the third display area.

The display screen generation unit may display a correspondence between the original data and the medical care period in an identifiable manner on the display screen.

The display screen generation unit may highlight, in a case where any of the medical care period is selected in the third display area, the original data corresponding to the selected medical care period in the second display area.

A request reception unit that receives a change request to change the extracted data constituting the medical care document, and a change unit that changes the extracted data according to the change request received by the request reception unit may be provided.

In a case where the above change is made by replacing unchanged data before the change with changed data after the change, by selecting the extracted data displayed in the first display area, the selected extracted data may be selected as the unchanged data, and by selecting the medical care period displayed in the third display area, the medical care data acquired at the selected medical care period may be selected as the changed data.

A change content learning unit that reflects a content of the change in a generation algorithm used by the medical care document generation unit to generate the medical care document may be provided.

The medical care document generation unit may generate the medical care document by using a generation algorithm corresponding to a type of the medical care document generated from the generation algorithm constructed for each type of the medical care document.

With the medical care support device according to the aspect of the present disclosure, even though the information used for the medical care document is automatically extracted, the extraction source of the extracted information becomes clear.

DESCRIPTION OF THE PREFERRED EMBODIMENTS

First Embodiment

Figure 1:
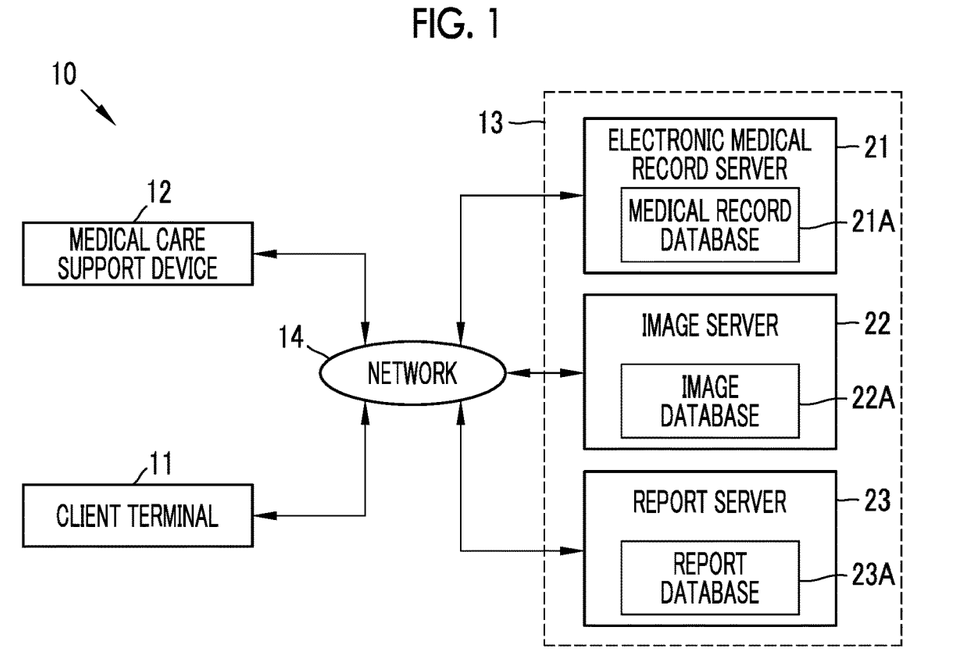
FIG. 1 is an explanatory diagram showing a configuration of a medical care support system.

As shown in FIG. 1, a medical care support system 10 is a computer system that provides medical care support in a medical facility such as a hospital, and comprises a client terminal 11, a medical care support device 12, and a server group 13. These elements constituting the medical care support system 10 are connected to each other so as to be able to communicate with each other by using a network 14 such as a local area network (LAN) installed in the medical facility.

The client terminal 11 is a terminal for receiving a service (a function of the medical care support device 12) from the medical care support device 12, and is a computer directly operated by a medical staff such as a doctor, a laboratory technician, or a nurse (including the case of a tablet terminal, etc.), or the like. The client terminal 11 is installed in a medical department such as an internal medicine or a surgery, various examination departments such as a radiological examination department or a clinical examination department, a nurse center, a reception desk, accounting, or other necessary places. Further, the client terminal 11 can be provided for each medical staff, and can be shared by a plurality of medical staff.

Figure 2:
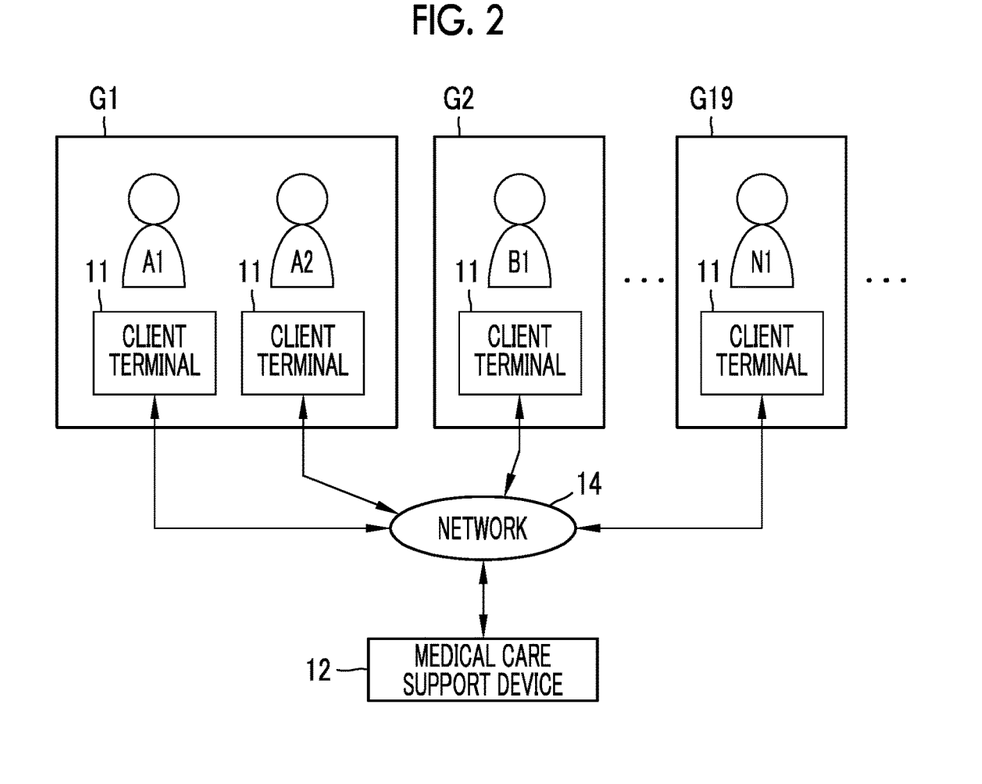
FIG. 2 is an explanatory diagram showing a client terminal included in the medical care support system.

Therefore, as shown in FIG. 2, the medical care support system 10 includes a plurality of client terminals 11. For example, a group G1 is an "internal medicine" to which a doctor A1 and a doctor A2 belong, and the doctor A1 and the doctor A2 each have a client terminal 11. Similarly, for example, a group G2 is a "surgery" to which a doctor B1 belongs, and the group G2 has at least one client terminal 11. Further, for example, a group G19 is a "radiology department" to which a technician N1 belongs, and the group G19 has at least one client terminal 11.

The medical care support device 12 provides the client terminal 11 with a display screen including medical care data, for example, in response to a request from the client terminal 11. The medical care support device 12 acquires medical care data to be used on the display screen from the server group 13.

Medical care data is data related to the medical care of a patient, and more specifically, images, reports, examination results, and other medical care processes acquired or generated in medical examinations, tests, surgeries, and the like. Alternatively, it is data obtained as a result of medical care, or information indicating the location of these, so-called links (aliases), and the like. In addition, one piece of medical care data may be composed of only one of the above-mentioned images, reports, examination results, etc. (for example, only one image), and one piece of medical care data may be composed by combining a plurality of the above-mentioned images, reports, examination results, etc. (for example, a plurality of images obtained by one examination and one report). That is, one piece of medical care data may be composed of a collection of a plurality of pieces of medical care data.

A display screen provided by the medical care support device 12 to the client terminal 11 refers to data used by the client terminal 11 to form a screen of a display unit 36 (see FIG. 3) of the client terminal 11. Further, the display screen provided by the medical care support device 12 to the client terminal 11 includes not only data for full-screen display that the client terminal 11 constitutes the display of the entire screen but also data that constitutes the display related to a part of the screen. For example, in the present embodiment, the medical care support device 12 provides the client terminal 11 with a display screen that can be displayed in a general window format on a part of the screen of the display unit 36.

Specifically, the display screen provided by the medical care support device 12 to the client terminal 11 is a medical care document display screen (see FIG. 9) for displaying medical care documents. Medical care documents are various types of medical care documents such as an inpatient medical care plan showing the medical care schedule of a patient scheduled to be hospitalized, a discharge summary that is a summary of medical care performed during hospitalization (see FIGS. 7 and 8), a medical care information provision document that also functions as a referral letter to another medical institution, medical certificates submitted for insurance coverage, various publicly funded documents, and the like. For example, a medical care document display screen 90 shown in FIG. 9 shows an example in which the medical care document is a discharge summary 70 shown in FIGS. 7 and 8. The medical care document is a layout of extracted data extracted from the medical care data in a predetermined format. Each of the extracted data constituting the medical care document is, for example, medical care data such as an image obtained by an examination (medical care) or a report generated in accordance with the examination (medical care). In addition, these extracted data may include all (whole) of one piece of medical care data, or may contain only a part of one piece of medical care data. In the former case, for example, it may be all areas of one image or the whole of one report. In the latter case, for example, it may be a partial area of an image clipped from one image, or a part of a report extracted from one report.

The medical care support device 12 provides a display screen to the client terminal 11 in a description format using a markup language such as extensible markup language (XML) data, for example. The client terminal 11 displays an XML format display screen using a web browser. The medical care support device 12 can provide a display screen to the client terminal 11 in another format such as JavaScript (registered trademark) object notation (JSON) instead of XML.

The server group 13 searches for medical care data in response to the request from the medical care support device 12, and provides the medical care data corresponding to the request to the medical care support device 12. The server group 13 includes an electronic medical record server 21, an image server 22, a report server 23, and the like.

The electronic medical record server 21 has a medical record database 21A for storing electronic medical records. An electronic medical record is a collection of one or a plurality of pieces of medical care data. Specifically, the electronic medical record includes, for example, medical care data such as a medical examination record, a result of a specimen test, a patient's vital sign, an order for tests, a treatment record, or accounting data. The electronic medical record can be input and viewed using the client terminal 11.

A medical examination record is a record of the contents and results of the interview or palpation, the disease name, or the like. A specimen is blood or tissue collected from a patient, or the like, and a specimen test is a blood test, a biochemical test, or the like. A vital sign is data indicating a patient's condition such as a patient's pulse, blood pressure, or body temperature. An order for examinations is a request for examinations such as a specimen test, photography using various modality, report generation, treatment or surgery, medication, or the like. A treatment record is a record of treatment, surgery, medication, prescription, or the like. Accounting data is data related to consultation fees, drug fees, hospitalization fees, and the like.

The image server 22 is a so-called PACS (picture archiving and communication system) server, and has an image database 22A in which examination images are stored. An examination image is an image obtained by various image examinations such as computed tomography (CT) examination, magnetic resonance imaging (MRI) examination, X-ray examination, ultrasonography, and endoscopy. These examination images are recorded in a format conforming to, for example, the digital imaging and communications in medicine (DICOM) standard. The examination image can be viewed using the client terminal 11.

The report server 23 has a report database 23A for storing an interpretation report. An interpretation report (hereinafter simply referred to as a report) is a report that summarizes the interpretation results of the examination image obtained by the image examination. The interpretation of the examination image is performed by a radiologist. The report can be generated and/or viewed using the client terminal 11.

A patient ID is attached to each of the above electronic medical records, examination images, and reports. In addition to the patient ID, information that identifies the medical staff who input the medical care data for each piece of medical care data is attached to the electronic medical record. In addition to the patient ID, information that identifies the medical staff (specifically, the laboratory technician) who performed the examination is attached to the examination image. Information that identifies the medical staff (specifically, the radiologist) that generated the report is attached to the report. Information that identifies the medical staff is an ID such as the name of the medical staff or a unique number and/or symbol given to each medical staff (hereinafter referred to as a medical staff ID).

The client terminal 11, the medical care support device 12, and the servers 21 to 23 constituting the server group 13 are configured by installing an operating system program and an application program such as a server program or a client program based on a computer such as a server computer, a personal computer, or a workstation. That is, the basic configurations of the client terminal 11, the medical care support device 12, and the servers 21 to 23 constituting the server group 13 are the same, and a central processing unit (CPU), a memory, a storage, a communication unit, etc., and a connection circuit for connecting these are provided. The communication unit is a communication interface (LAN port or the like) for connecting to the network 14. The connection circuit is, for example, a motherboard that provides a system bus and/or a data bus and the like.

Figure 3:
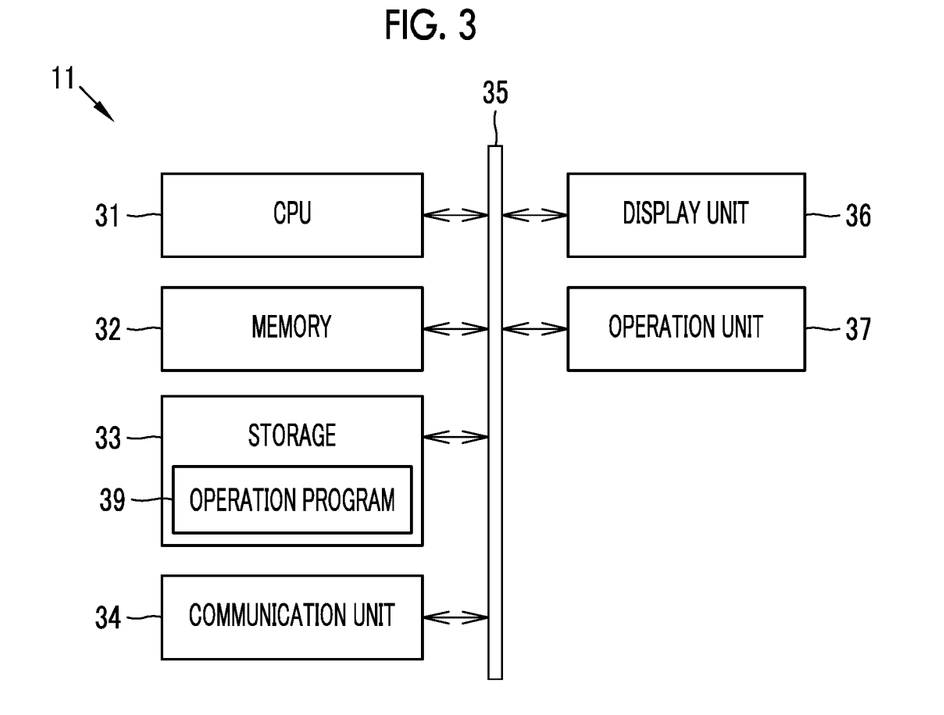
FIG. 3 is a block diagram showing a configuration of a client terminal.

As shown in FIG. 3, the client terminal 11 comprises a display unit 36 and an operation unit 37 in addition to a CPU 31, a memory 32, a storage 33, a communication unit 34, and a connection circuit 35. The display unit 36 is, for example, a display using a liquid crystal display or the like, and has at least a screen for displaying a display screen provided by the medical care support device 12. The operation unit 37 is, for example, a pointing device such as a mouse and/or an input device such as a keyboard. The display unit 36 and the operation unit 37 can form a so-called touch panel.

The client terminal 11 stores an operation program 39 in addition to the operating system program and the like in the storage 33. The operation program 39 is an application program for receiving the function of the medical care support device 12 by using the client terminal 11. In the present embodiment, the operation program 39 is a web browser program. Here, the operation program 39 can be a dedicated application program for receiving the function of the medical care support device 12. The operation program 39 may include one or a plurality of gadget engines for controlling a part or all of the display screen provided by the medical care support device 12. A gadget engine is a subprogram that exhibits various functions by operating alongside a web browser or the like.

Figure 4:
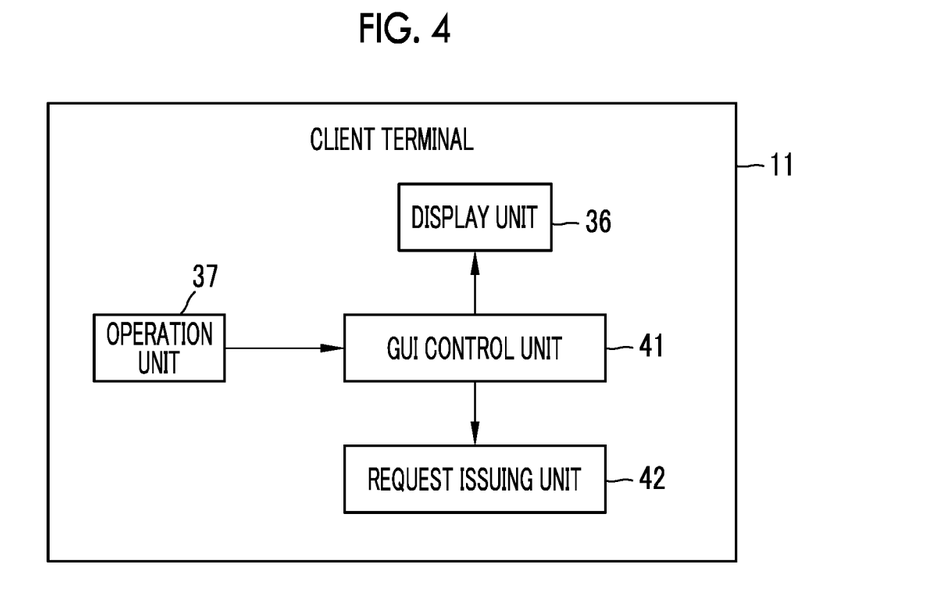
FIG. 4 is a block diagram showing a function of the client terminal.

In a case where the operation program 39 is activated in the client terminal 11, as shown in FIG. 4, the CPU 31 of the client terminal 11 functions as a graphical user interface (GUI) control unit 41 and a request issuing unit 42 in cooperation with the memory 32.

The GUI control unit 41 displays the display screen provided by the medical care support device 12 on the web browser in the display unit 36. The GUI control unit 41 controls the client terminal 11 in response to an operation instruction input using the operation unit 37, such as a button click operation with a pointer.

The request issuing unit 42 issues various processing requests (hereinafter referred to as processing requests) to the medical care support device 12 in response to the operation instruction of the operation unit 37. The processing request issued by the request issuing unit 42 is, for example, a distribution request for the display screen, an edit request for the display screen, or the like. The request issuing unit 42 transmits the processing request to the medical care support device 12 via the communication unit 34 and the network 14.

The distribution request for the display screen is for requesting the medical care support device 12 to distribute a display screen having a specific configuration. In the present embodiment, the medical care document display screen can be distributed by the distribution request for the display screen for displaying the designated type of medical care document. For example, in response to a distribution request for a display screen (medical care document display screen) for displaying a discharge summary (see FIGS. 7 and 8) as a medical care document, a medical care document display screen (see FIG. 9) for displaying the discharge summary can be distributed.

The edit request for the display screen is for requesting the medical care support device 12 to edit (change) the contents of the medical care data and the like to be displayed on the display screen after receiving the distribution of the display screen having a specific configuration from the medical care support device 12. The edit request includes not only a request to change a part or all of the data constituting the display screen and/or to change the data layout, and but also a request to change a part or all of the data (extracted data) constituting the medical care document displayed on a medical care document display screen, and/or to change the layout of the extracted data, for example, in a case where the display screen is the medical care document display screen. That is, the edit request also includes a change request of the present disclosure, which requests a change of the extracted data constituting the medical care document.

The distribution request and/or edit request for the display screen includes information such as a medical staff ID and an address on the network of the client terminal 11. The medical staff ID is entered on a login screen (not shown) for the medical care support system 10 (or the medical care support device 12).

Figure 5:
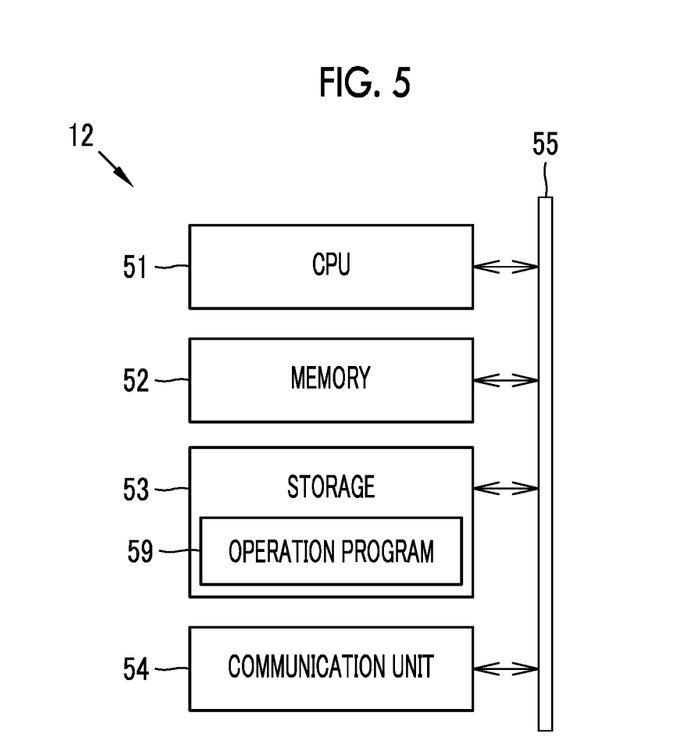
FIG. 5 is a block diagram showing a configuration of a medical care support device.

As shown in FIG. 5, the medical care support device 12 comprises a CPU 51, a memory 52, a storage 53, a communication unit 54, and a connection circuit 55. The medical care support device 12 may comprise a display unit and/or an operation unit in the same manner as the client terminal 11 as necessary. Further, although a display unit and/or an operation unit can be attached as necessary, in the present embodiment, the medical care support device 12 does not have a display unit and an operation unit.

Figure 6:
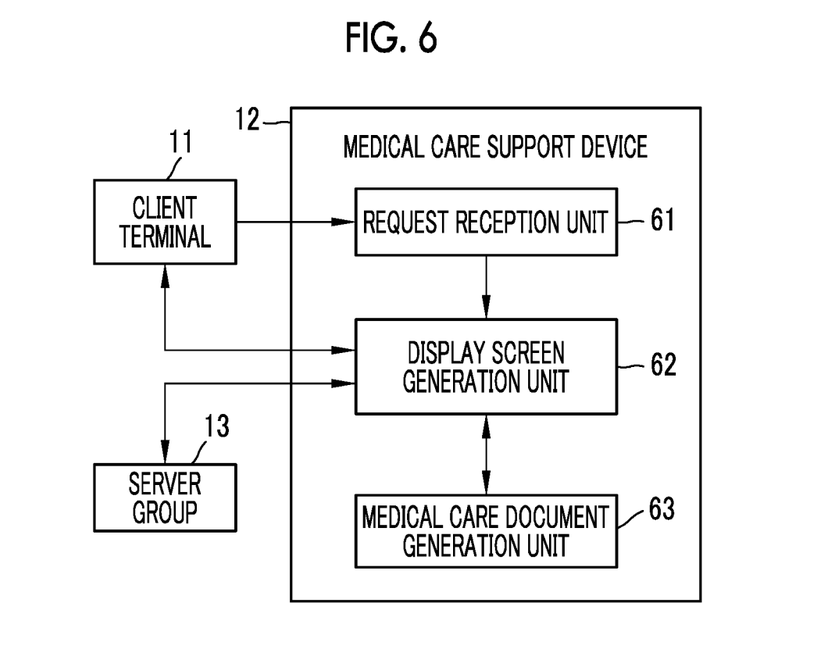
FIG. 6 is a block diagram showing a function of the medical care support device.

The medical care support device 12 stores an operation program 59 in addition to the operating system and the like in the storage 53. The operation program 59 is an application program for causing the computer constituting the medical care support device 12 to function as the medical care support device 12. In a case where the operation program 59 is activated, as shown in FIG. 6, the CPU 51 of the medical care support device 12 functions as a request reception unit 61, a display screen generation unit 62, a medical care document generation unit 63, and the like in cooperation with the memory 52.

The request reception unit 61 receives various processing requests such as a distribution request and an edit request for the display screen from the client terminal 11. In a case where the request reception unit 61 receives various processing requests, the request reception unit 61 inputs a processing instruction to each unit that executes the corresponding processing according to the content of the requested processing. For example, in a case where there is a distribution request for the display screen from the client terminal 11, the request reception unit 61 inputs a generation instruction of the corresponding display screen to the display screen generation unit 62. Similarly, in a case where there is an edit request for the display screen from the client terminal 11, the request reception unit 61 inputs an edit instruction of the corresponding display screen to the display screen generation unit 62. The request reception unit 61 also receives a request to log in to the medical care support device 12, and a login processing unit (not shown) executes login processing such as confirmation of the medical staff ID and password.

The display screen generation unit 62 generates or edits various display screens such as the medical care document display screen (see FIG. 9). Specifically, XML data representing various display screens is generated or the generated XML data is edited. The display screen generation unit 62 accesses the server group 13, the client terminal 11, or another device or system that is linked with the medical care support system 10 as necessary, and acquires medical care data used for generating or editing the display screen. The display screen generation unit 62 can hold a part or all of the medical care data acquired from the server group 13 or the like in order to reduce the access frequency to the server group 13 or the like.

The medical care document generation unit 63 generates a medical care document according to an instruction from the display screen generation unit 62. In a case where the display screen generation unit 62 generates a medical care document display screen for displaying a medical care document as a display screen, the display screen generation unit 62 inputs an instruction to generate a medical care document to be displayed on the medical care document display screen to the medical care document generation unit 63. The medical care document generation unit 63 generates a medical care document of a designated type according to this instruction. The medical care document generation unit 63 accesses the server group 13, the client terminal 11, or another device or system that is linked with the medical care support system 10 as necessary, and acquires medical care data (extracted data) used for generating the medical care document. Further, the medical care document generation unit 63 can hold a part or all of the medical care data (extracted data) acquired from the server group 13 or the like in order to reduce the access frequency to the server group 13 or the like. Of course, the medical care document generation unit 63 can hold a part or all of the generated medical care document.

Figure 7:
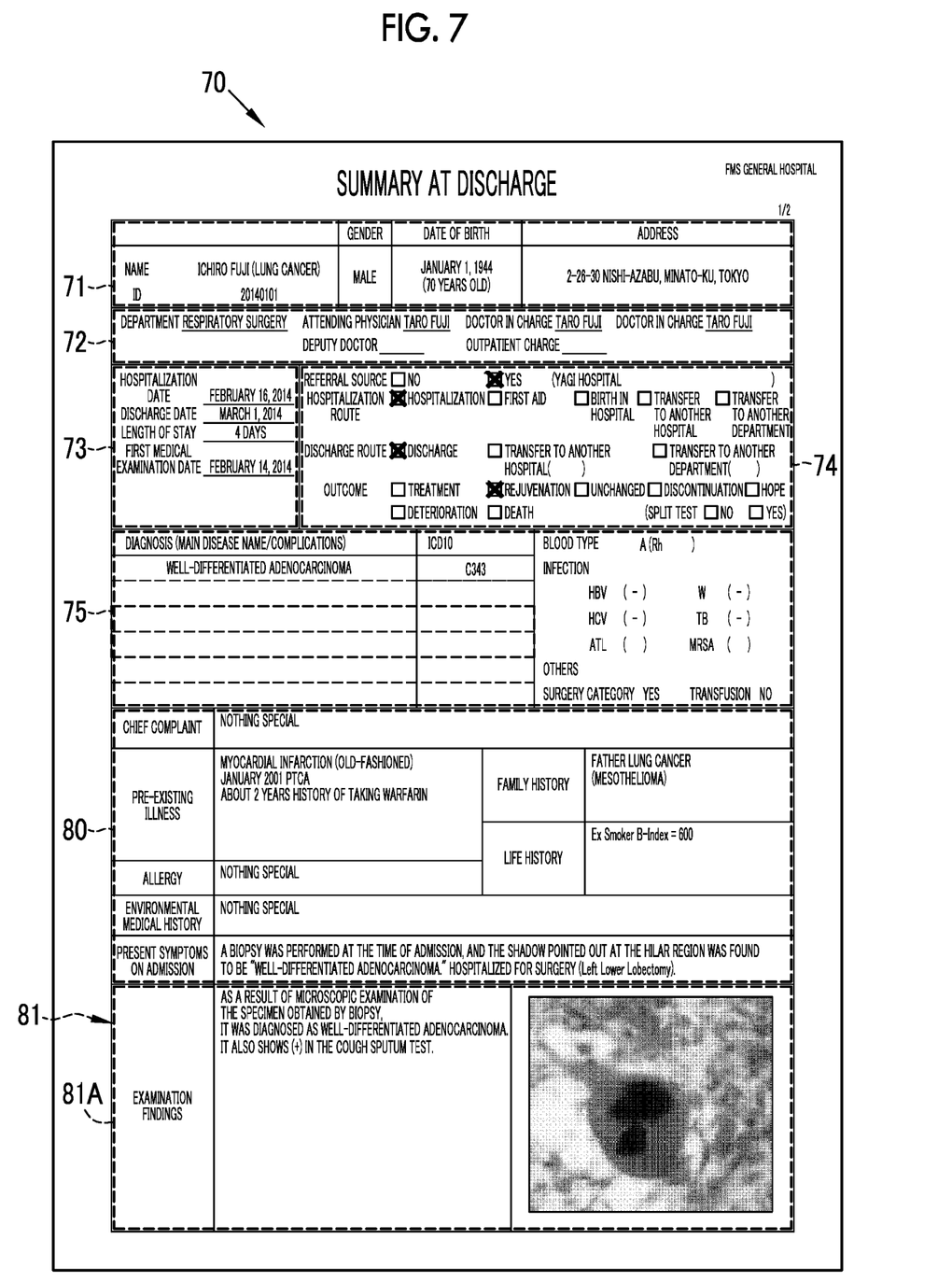
FIG. 7 is an explanatory diagram of a discharge summary.
Figure 8:
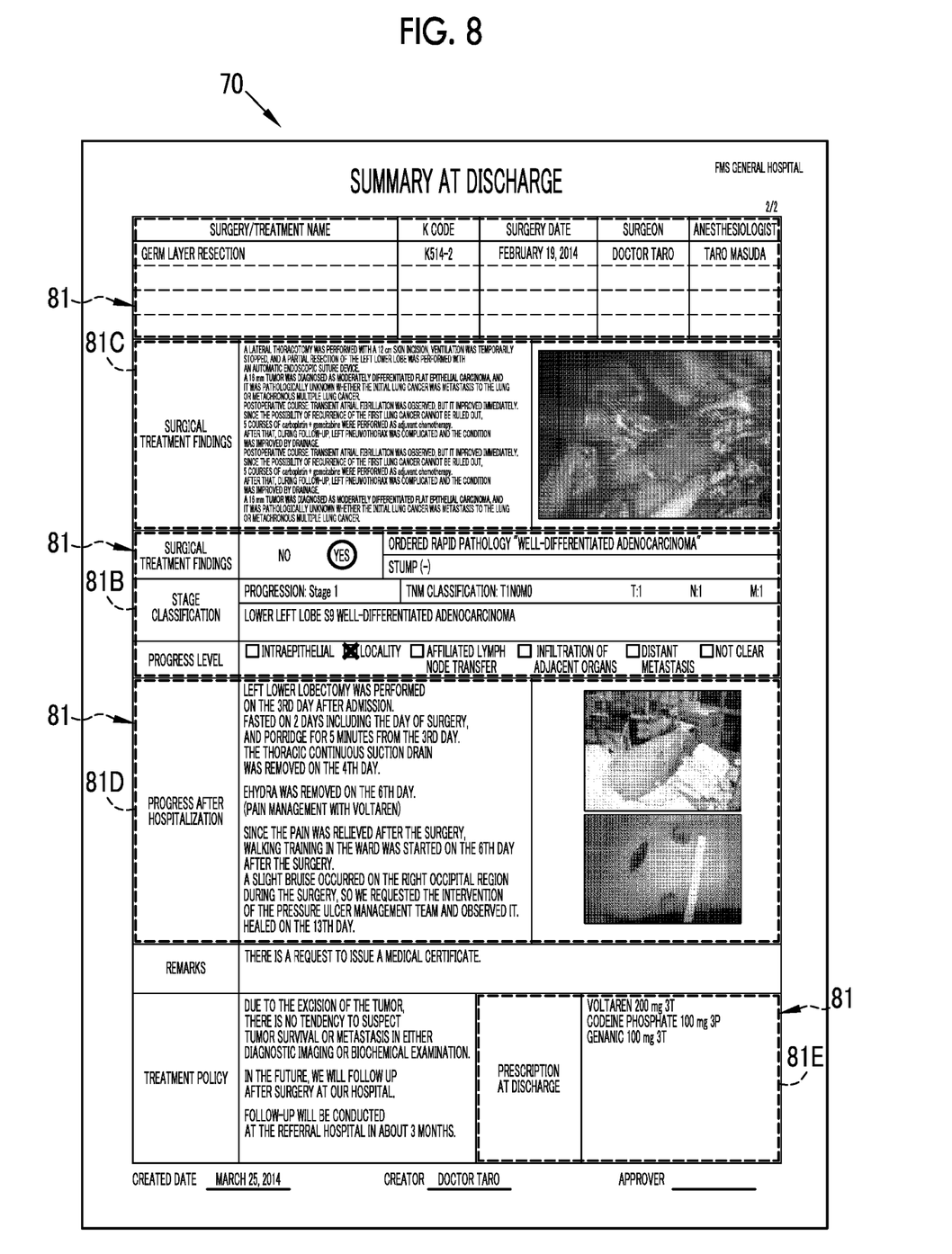
FIG. 8 is an explanatory diagram of a discharge summary.
Figure 9:
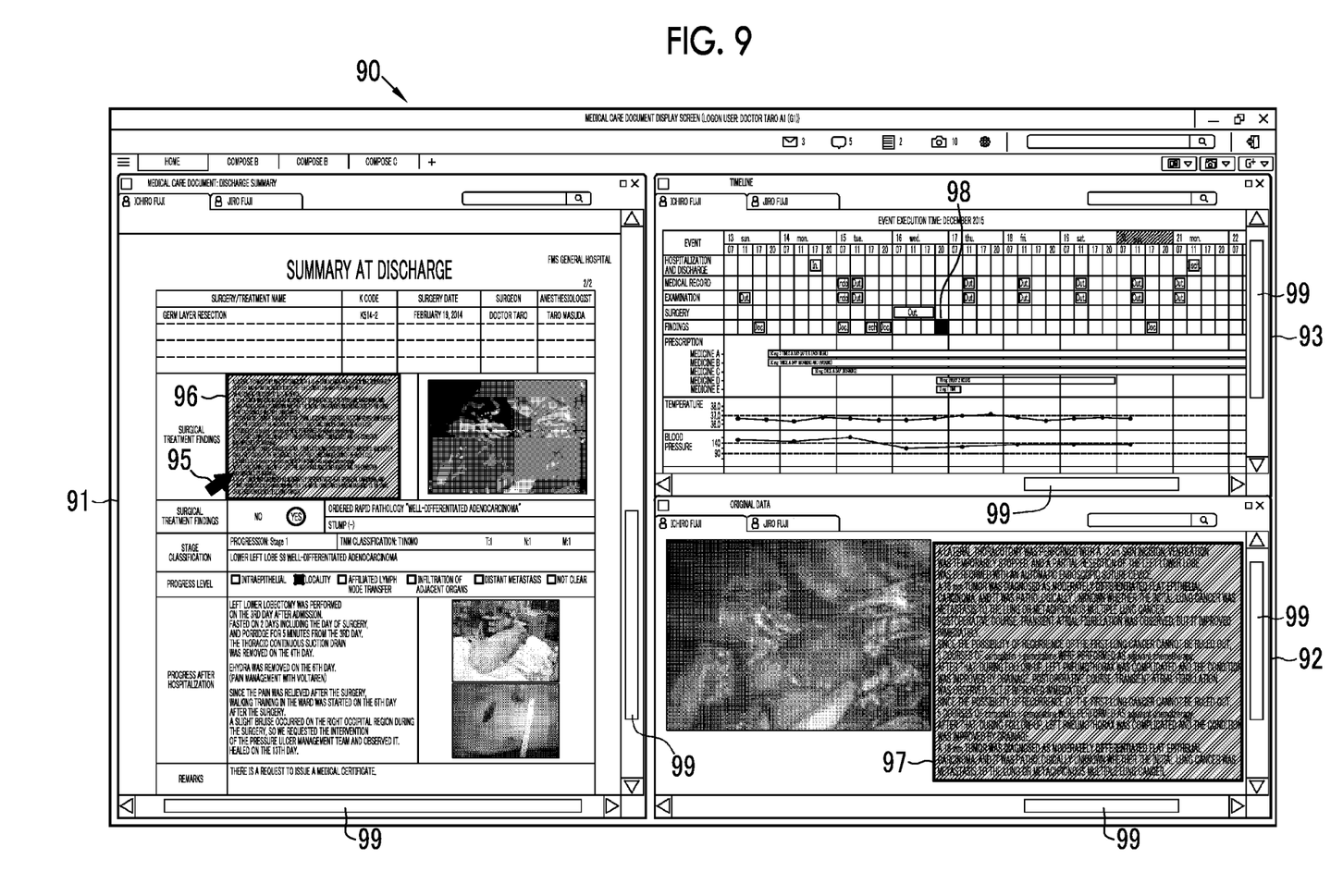
FIG. 9 is an explanatory diagram of a medical care document display screen.

The medical care document generation unit 63 generates, for example, the discharge summary 70 shown in FIGS. 7 and 8 as a medical care document. The discharge summary 70 is a medical care document issued in the case where an inpatient is discharged from the hospital, and is a summary of information regarding medical care from the hospitalization to the discharge of the patient. The discharge summary 70 is provided with a patient basic information display field 71, a user information display field 72, a hospitalization information display field 73, a referral information display field 74, a patient profile display field 75, a medical record information display field 80, and an examination/treatment content display field 81.

In the patient basic information display field 71, the patient's basic information such as the patient's name, gender, date of birth, and address is displayed. In the user information display field 72, information on the hospital side such as the medical department, an attending physician, and a doctor in charge, which perform medical care on a patient is displayed. In the hospitalization information display field 73, information regarding hospitalization/discharge such as hospitalization date, discharge date, and number of hospitalization days is displayed. In the referral information display field 74, a method related to referral such as presence or absence of a referral source, hospitalization route, discharge route, etc. is displayed. In the patient profile display field 75, a patient profile such as a main disease name and complications is displayed.

Further, in the medical record information display field 80, information extracted from the patient's past to present medical records, such as chief complaints, pre-existing diseases, and allergies, is displayed. Further, in the examination/treatment content display field 81, information regarding the content of the examination and treatment is displayed. In the present embodiment, the examination/treatment content display field 81 is further provided with examination fields 81A and 81B for displaying information regarding the examination, a surgery field 81C for displaying the information regarding the surgery, a finding field 81D for displaying information regarding the findings, and a prescription field 81E for displaying information regarding the prescription.

Among these fields 71 to 75, 80, and 81 (81A to 81E), the extraction source of the information displayed in the fields 71 to 75 is predetermined, including the information to be displayed in each item in each field. Further, the layout of the fields 71 to 75 is predetermined, including the layout of each item in each field. Therefore, the medical care document generation unit 63 uniquely extracts the information to be displayed in the fields 71 to 75 from the predetermined extraction source as predetermined according to the type of field and/or the type of item in the field, or generates the fields 71 to 75 of the discharge summary 70 by uniquely laying out the document as predetermined.

On the other hand, the information displayed in the fields 80 and 81 (81A to 81E) has a plurality of extraction sources, and/or the amount of information of the extraction source is larger than the amount that can be displayed in the fields 80 and 81. In addition, the content of each item in the field also differs depending on the type of information of the extraction source and the like. Further, the layout of the fields 80 and 81 and the layout of each item in each field also differ depending on the type of information of the extraction source and the like. That is, for the information displayed in the fields 80 and 81, it is necessary to select the extraction source, the extraction site (which part of the information is to be extracted and how much), and the layout of the extracted information. Therefore, the medical care document generation unit 63 determines the extraction source and extraction site of the information to be displayed in the fields 80 and 81 and each item in each field by a generation algorithm for discharge summary generation constructed by learning a plurality of generated discharge summaries as learning data, and extracts the information. Further, the medical care document generation unit 63 lays out the information to be displayed in the fields 80 and 81 and each item in each field (that is, the extracted information (extracted data)) by the generation algorithm described above. Thereby, the fields 80 and 81 of the discharge summary 70 are generated.

In this way, for the fields (fields 80 and 81 in the above embodiment) in which any one of the extraction source, the extraction site, and the layout cannot be uniquely determined, the medical care document generation unit 63 generates the generated medical care document by a generation algorithm constructed as learning data (generates the generated medical care document by so-called trained artificial intelligence (AI)). In this way, the field in which any one of the extraction source, the extraction site, and the layout cannot be uniquely determined differs depending on the type of medical care document. Therefore, a generation algorithm for generating a field that cannot be uniquely determined in this way is constructed for each type of the medical care document. The medical care document generation unit 63 uses a generation algorithm corresponding to the type of medical care document in the case of generating a field that cannot be uniquely determined. Although a case where some of the fields of the medical care document are generated by the so-called trained AI has been described as an example, all the fields of the medical care document may be generated by the trained AI.

The display screen generation unit 62 generates a medical care document display screen using a medical care document such as the discharge summary 70 generated by the medical care document generation unit 63. For example, as shown in FIG. 9, the medical care document display screen 90 for displaying the discharge summary 70 as a medical care document has a first display area 91 for displaying a medical care document (in this example, the discharge summary 70), a second display area 92 for displaying original data of the extracted data (the medical care data of the extraction source of the extracted data) constituting the medical care document displayed in the first display area 91, and a third display area 93 for displaying a medical care period in which the medical care related to the acquisition of the medical care data is performed in time series, for the same patient as the extracted data and the original data.

Then, on the display screen (medical care document display screen 90 in the example of FIG. 9), the display screen generation unit 62 displays a correspondence between the extracted data of the first display area 91, the original data of the second display area 92, and the medical care period of the third display area 93 in an identifiable manner. That is, the display screen generation unit 62 generates a display screen in which the correspondence described above can be identified. A medical care period in which medical care related to the acquisition of medical care data is performed is, for example, a period in which an examination A is performed (a period in which an examination A related to the acquisition of examination data A is performed (day or date and time)) in a case where the examination A is performed as medical care and the examination data A is acquired as medical care data by the examination A.

As a specific mode for displaying a correspondence between the extracted data and the original data in an identifiable manner, for example, in a case where any of the extracted data displayed in the first display area 91 is selected, the original data of the selected extracted data can be highlighted in the second display area 92. The extracted data can be selected, for example, by placing a cursor on any of the extracted data and clicking with the cursor placed on the extracted data, or by designating an item such as data selection in a window displayed in a pop-up by clicking (right-clicking, etc.) with the cursor placed on the extracted data. In addition, highlighting is possible by surrounding the original data of the selected extracted data in a frame, blinking the original data of the selected extracted data, making the background color and/or display color of the original data of the selected extracted data different from other original data, displaying a mark or the like on top of the original data of the selected extracted data, and the like.

Further, it may be possible to identify a correspondence between extracted data and original data by, for example, attaching a common mark on extracted data and original data of the extracted data, such as attaching a common mark "○" to extracted data A and original data A of the extracted data A, and attaching a common mark "Δ" to the extracted data B and the original data B of the extracted data B, surrounding extracted data and original data of the extracted data in a frame of a common form, making a display mode (background color, display color, and/or lighting (blinking) mode, etc.) of extracted data and original data of the extracted data common, or the like. In this way, by providing a common part in the display form of extracted data and original data of the extracted data so that the correspondence can be identified, it is possible to identify the correspondence between the extracted data and the original data without selecting the extracted data. Furthermore, by connecting extracted data and original data of the extracted data with a line segment (displaying a linear index (mark) connecting extracted data and original data of the extracted data) or the like, it may be possible to identify the correspondence between the extracted data and the original data without selecting the extracted data. Of course, in a case where any of the extracted data is selected, by providing a common part in the display form of extracted data and original data of the extracted data, and/or by connecting extracted data and original data of the extracted data with a line segment or the like, it may be possible to identify the correspondence between the extracted data and the original data.

In a case where the extracted data is a part of the original data extracted (for example, a part of one image or a part of a series of sentences), the portion of the original data extracted as the extracted data may be highlighted or the like so that which portion of the original data corresponds to the extracted data can be displayed in an identifiable manner. Further, in the present embodiment, the configuration has been described in which the original data of the extracted data displayed in the first display area 91 is displayed in the second display area 92, but in the second display area 92, not only the original data but also all the medical care data of the same patient as the original data may be displayed. Further, a fourth display area may be provided, and medical care data other than the original data among the medical care data of the same patient as the original data may be displayed in the fourth display area. Further, in the present embodiment, a plurality of pieces of original data are displayed in the second display area 92, but only one piece of original data corresponding to the selected extracted data may be displayed in the second display area 92. Further, information indicating the location of the original data instead of the original data or together with the original data (for example, a link to the storage source, a terminal name of the storage source, a directory name, a folder name, etc.) may be displayed in the second display area 92.

A specific mode for displaying a correspondence between the extracted data and the medical care period in an identifiable manner can be configured in the same manner as described above. That is, in a case where the extracted data is selected, the medical care period of the selected extracted data may be highlighted in the third display area 93. Further, by providing a common part in the display form of the extracted data and the medical care period of the extracted data, it may be possible to identify the correspondence between the extracted data and the medical care period. Further, by connecting the extracted data and the medical care period with a line segment or the like, it may be possible to identify the correspondence between the extracted data and the medical care period.

A specific mode for displaying a correspondence between the original data and the medical care period in an identifiable manner can be configured in the same manner as described above. That is, in a case where either one of the original data and the medical care period is selected, the other data (original data or medical care period) corresponding to the selected one may be highlighted. Further, by providing a common part in the display form of the original data and the medical care period, it may be possible to identify the correspondence between the original data and the medical care period. Further, by connecting the original data and the medical care period with a line segment or the like, it may be possible to identify the correspondence between the original data and the medical care period.

A specific mode for displaying all correspondences between the extracted data, the original data, and the medical care period in an identifiable manner can be configured in the same manner as described above. That is, in a case where any one of the extracted data, the original data, and the medical care period is selected, the remaining two may be highlighted. Further, by providing a common part in the display form of the extracted data, the original data, and the medical care period, it may be possible to identify the correspondence between the extracted data, the original data, and the medical care period. Further, by connecting the extracted data, the original data, and the medical care period with a line segment or the like, it may be possible to identify the correspondence between the extracted data, the original data, and the medical care period.

In this way, the display screen generation unit 62 displays a correspondence between the extracted data, the original data, and the medical care period in an identifiable manner on the medical care document display screen 90. For example, in the example of FIG. 9, extracted data of a destination to which a cursor 95 is moved is treated as being selected, and the extracted data is surrounded by, for example, a green square frame 96. Further, original data corresponding to the selected extracted data (extracted data surrounded by the frame 96) is surrounded by a green square frame 97 having the same mode as the frame 96. Further, a medical care period corresponding to the extracted data surrounded by the frame 96 is surrounded by a green square frame 98 similar to the frames 96 and 97. Thereby, a correspondence between the extracted data, the original data, and the medical care period is displayed in an identifiable manner. Further, in the example of FIG. 9, the selected extracted data, the original data corresponding to the selected extracted data, and the medical care period corresponding to the selected extracted data are colored in a common color (for example, blue), which also makes it possible to identify the correspondence between the extracted data, the original data, and the medical care period.

In the example of FIG. 9, in the third display area 93, all the medical care periods in which the medical care related to the acquisition of medical care data is performed are displayed for the same patient as the extracted data. However, among the medical care periods in which the medical care related to the acquisition of medical care data is performed, only the medical care period in which the medical care related to the acquisition of the extracted data displayed in the first display area 91 is performed may be displayed in the third display area 93. Further, in the example of FIG. 9, in the third display area 93, in addition to the medical care period, vital information of the patient (body temperature and blood pressure in the present embodiment) is also displayed in time series. However, another medical care data (for example, vital information such as pulse and/or medical care data other than vital information (for example, examination data such as blood glucose level)) or the like may be displayed. Of course, in the third display area 93, only the medical care period may be displayed without displaying vital information or the like.

The display screen generation unit 62 distributes the display screen generated as described above to the client terminal 11 via the communication unit 54. Thereby, the client terminal 11 displays the display screen provided by the display screen generation unit 62 on the display unit 36.

Further, the display screen generation unit 62 edits the display screen according to the edit request for the display screen input from the client terminal 11. As described above, the edit request for the display screen is for requesting the editing (change) of the contents of the medical care data and the like to be displayed on the display screen, and includes, for example, a request to change a part or all of the extracted data constituting the discharge summary 70 displayed on the medical care document display screen 90, or to change the layout of the extracted data. The edit request is input from the operation unit 37 of the client terminal 11 via the GUI, for example. It is preferable that the edit request is made by operating the display screen or the like in a state where the medical care document display screen 90 is displayed.

Specifically, in the case of changing the extracted data constituting the discharge summary 70 displayed on the medical care document display screen 90, first, extracted data to be changed (hereinafter referred to as unchanged data) is selected and an instruction to change the unchanged data is given. The selection of the unchanged data and the instruction of the change are performed, for example, by moving the cursor 95 onto the unchanged data (selecting the unchanged data) and selecting a data change from an edit menu displayed by right-clicking (an instruction to change the unchanged data) in the first display area 91. Next, data to be replaced (hereinafter referred to as changed data) is selected as a substitute for the unchanged data. The changed data is selected, for example, by moving the cursor 95 on the medical care period of the medical care that triggered the acquisition of the changed data and performing a click operation (the medical care period is selected such that the medical care data acquired at the selected medical care period is selected as the changed data) in the third display area 93. In this way, in a case where the selection of the unchanged data, the instruction of the change, and the selection of the changed data are performed, an edit request (change request) to replace the unchanged data with the changed data is issued by the request issuing unit 42.

The edit request issued as described above is received by the request reception unit 61, and the edit instruction according to the edit request is input from the request reception unit 61 to the display screen generation unit 62. The display screen generation unit 62 edits the display screen such as changing the extracted data constituting the discharge summary 70 according to this edit instruction, that is, the edit request input from the client terminal 11, and distributes the edited display screen to the client terminal 11. In this way, the display screen generation unit 62 also functions as a change unit of the present disclosure, which changes the extracted data according to a change request to change the extracted data constituting the medical care document.

In addition, although an example in which the medical care data acquired in the selected medical care period is selected as the changed data by selecting the medical care period displayed in the third display area 93 has been described, for example, the server group 13 may be accessed and the changed data may be selected from the data stored in the server group 13. Further, the changed data may be selected from the medical care data displayed in the above-mentioned fourth display area (that is, the area for displaying medical care data other than the original data among the medical care data of the same patient as the original data). Further, the changed data may be selected from the data displayed in the second display area 92.

Further, although an example in which the display screen generation unit 62 performs all the processing of editing (changing) the display screen has been described, for example, in a case where an edit (change) of the medical care document is requested on the display screen for displaying the medical care document (that is, the medical care document display screen), the display screen may be edited by causing the medical care document generation unit 63 to perform the edit (change) processing of the medical care document and causing the display screen generation unit 62 to perform processing of reflecting the medical care document edited (changed) by the medical care document generation unit 63 on the display screen.

The medical care support system 10 having the above configuration operates as follows. In a case where the medical staff logs in to the medical care support system 10 using the client terminal 11, designates a medical care document by the GUI of the client terminal 11 or the like, and makes a distribution request for a medical care document display screen, the display screen generation unit 62 instructs the medical care document generation unit 63 to generate the designated medical care document. The medical care document generation unit 63 generates a medical care document by extracting medical care data (extracted data) necessary for constructing the medical care document from the server group 13 and the like according to an generation algorithm corresponding to the designated type of medical care document, and laying out the extracted data.

The display screen generation unit 62 generates a medical care document display screen including this medical care document by using the medical care document generated by the medical care document generation unit 63, and provides the screen to the client terminal 11. Thereby, the client terminal 11 displays the medical care document display screen on the screen of the display unit 36. For example, in a case where a discharge summary is designated as a medical care document and a distribution request for a medical care document display screen is made, the medical care document generation unit 63 generates, for example, the discharge summary 70 shown in FIGS. 7 and 8, and the display screen generation unit 62 generates, for example, the medical care document display screen 90 including the discharge summary 70, as shown in FIG. 9. Then, the medical care document display screen 90 is displayed on the display unit 36.

In FIG. 9, the medical care document display screen 90 has a first display area 91 for displaying the discharge summary 70, a second display area 92 for displaying the original data of the extracted data constituting the discharge summary 70, and a third display area 93 for displaying the medical care period in which the medical care related to the acquisition of the extracted data and the original data is performed in time series. In the generation of the medical care document display screen 90, the display screen generation unit 62 displays the discharge summary 70 generated by the medical care document generation unit 63 in the first display area 91. Further, the display screen generation unit 62 displays the original data of the extracted data constituting the discharge summary 70 in the second display area 92. Further, the display screen generation unit 62 displays the medical care period of the medical care data of the same patient as the extracted data and the original data side by side in the third display area 93.

In each of the first to third areas 91 to 93, in a case where all the contents to be displayed do not fit in the area, a scroll bar 99 is displayed in the vicinity of the area. The scroll bar 99 is a GUI that is operated in a case where the display content of each of the first to third areas 91 to 93 is changed in the horizontal direction or the vertical direction and a non-display portion is displayed.

Further, the display screen generation unit 62 edits the medical care document display screen 90 in accordance with the operation of the client terminal 11 (movement of the cursor 95, click operation, drag operation, drop operation, operation via a GUI, etc.). In the example of FIG. 9, in a case where the cursor 95 is moved on any of the extracted data constituting the discharge summary 70 displayed in the first display area 91 and the extracted data is selected, the extracted data in the first display area 91, original data of the extracted data in the second display area 92, and a medical care period of the extracted data in the third display area 93 are surrounded by square frames 96, 97, and 98, respectively, and are colored with a common background color. Thereby, a correspondence between the extracted data, the original data, and the medical care period is displayed in an identifiable manner.

Further, in a case where an edit request (change request) to change a medical care document is made by an operation of the client terminal 11 or the like, the display screen generation unit 62 edits the display screen according to the change request. For example, in a case where a change request such as a change of the extracted data constituting the discharge summary 70 displayed on the medical care document display screen 90 is made, the display screen generation unit 62 edits the contents of the discharge summary 70 displayed on the medical care document display screen 90 according to the change request.

As described above, according to the aspect of the present disclosure, by providing the second display area 92 in the medical care document display screen 90 for displaying medical care documents and displaying the original data of the extracted data constituting the medical care document in the second display area 92, even though the extracted data is automatically extracted, for example, automatically extracted by a trained AI (generation algorithm), the extraction source of the extracted data becomes clear. In addition, by displaying the correspondence between the extracted data and the original data in an identifiable manner, the extraction source of each of a plurality of pieces of extracted data included in the medical care document is not confused, and the extraction source of the extracted data becomes clearer. Further, by providing the third display area 93 and displaying the medical care period in which the medical care related to the acquisition of the medical care data is performed, the correspondence between the extracted data, the original data, and the medical care period can be grasped. In addition, by displaying the correspondence between the extracted data, the original data, and the medical care period in an identifiable manner, the correspondence between these can be grasped more clearly.

Second Embodiment

Figure 10:
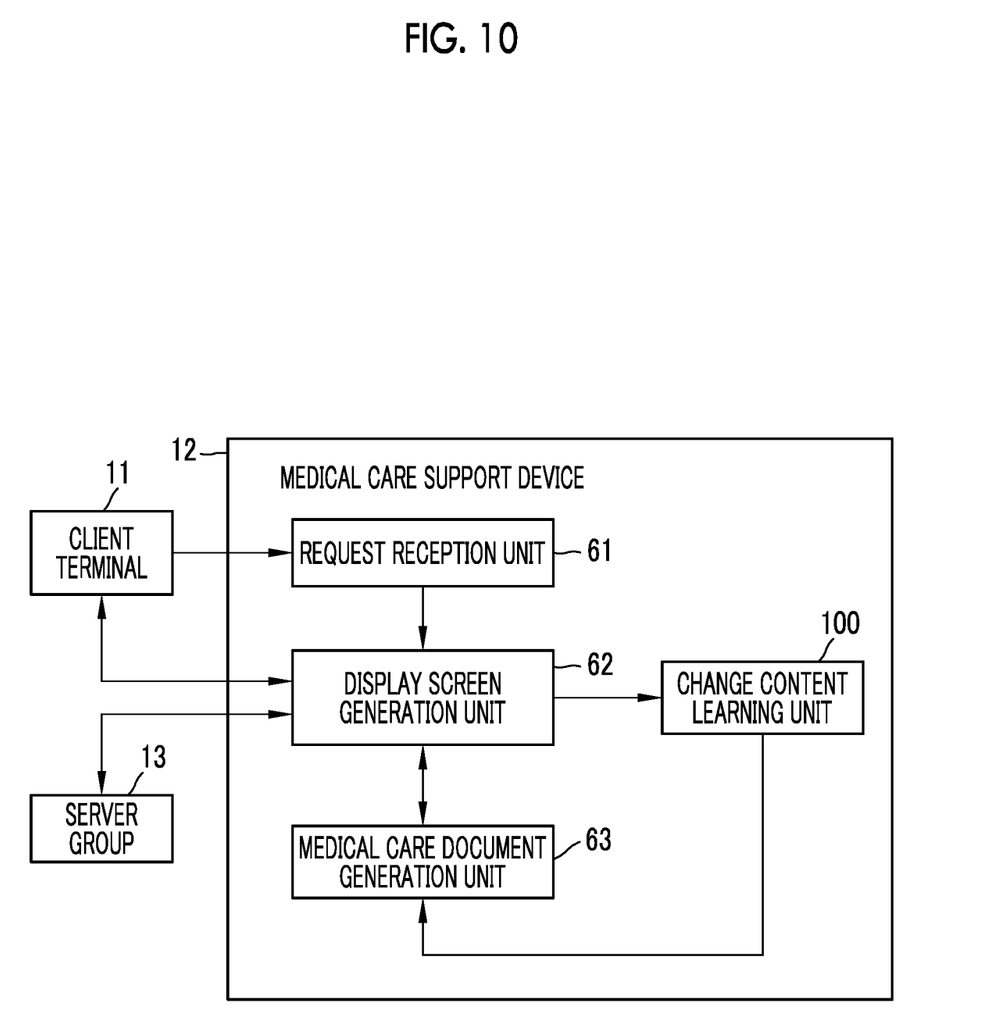
FIG. 10 is a block diagram showing a function of a medical care support device.

In the first embodiment, it is possible to edit the medical care document automatically generated by the medical care document generation unit 63 using the generation algorithm, such as changing the extracted data constituting the medical care document. However, as shown in FIG. 10, it is preferable to provide a change content learning unit 100 and reflect the result of the above-mentioned editing in the generation algorithm used by the medical care document generation unit 63. The change content learning unit 100 is one function of the operation program 59 (see FIG. 5), and the CPU 51 and the memory 52 cooperate to function as the change content learning unit 100. The generation algorithm is constructed by learning the generated medical care document as learning data. However, depending on the number, content, and/or other factors of the learning data, a desired mode of medical care document may not be generated. Therefore, as in the present embodiment, a generation algorithm capable of generating a medical care document closer to a desired mode is constructed by reflecting the edited medical care document which has become a medical care document of a desired mode by editing in the generation algorithm. Reflecting the edited medical care document in the generation algorithm means that reconstructing the generation algorithm by using the edited medical care document as new learning data and increasing the number of bases of the learning data, and/or reconstructing the generation algorithm by learning that the state before editing (change) is incorrect and the state after editing (change) is correct for the edited (changed) part.

In the first embodiment or the like, the client terminal 11 directly transmits a request for distribution/editing of a display screen such as the medical care document display screen 90 to the medical care support device 12, but it is also possible for the client terminal 11 to indirectly transmit a request for distribution/editing of the display screen via another device or system linked with the medical care support device 12. For example, since the client terminal 11 can operate the electronic medical record server 21, the client terminal 11 can operate the electronic medical record server 21, and transmit a request for distribution/editing of the display screen from the electronic medical record server 21 to the medical care support device 12. In this case, the medical care support device 12 generates and/or edits the display screen according to the request from the electronic medical record server 21, and distributes the display screen via the electronic medical record server 21 or directly to the client terminal 11.

The medical care support device 12 according to the first embodiment or the like comprises: the medical care document generation unit 63 that generates a medical care document (discharge summary 70) in which extracted data extracted from medical care data related to medical care of a patient is laid out in a predetermined format; and the display screen generation unit 62 that generates a display screen (medical care document display screen 90) having the first display area 91 for displaying the medical care document and the second display area 92 for displaying original data which is medical care data of an extraction source of the extracted data.

Further, the operation program 59 of the medical care support device 12 according to the first embodiment or the like causes the CPU 51 or the CPU 51 and the memory 52 to function as: the medical care document generation unit 63 that generates a medical care document (discharge summary 70) in which extracted data extracted from medical care data related to medical care of a patient is laid out in a predetermined format; and the display screen generation unit 62 that generates a display screen (medical care document display screen 90) having the first display area 91 for displaying the medical care document and the second display area 92 for displaying original data which is medical care data of an extraction source of the extracted data.

The operation method of the medical care support device 12 according to the first embodiment comprises: the medical care document generation step of generating, by the medical care document generation unit 63, a medical care document (discharge summary 70) in which extracted data extracted from medical care data related to medical care of a patient is laid out in a predetermined format; and the display screen generation step of generating, by the display screen generation unit 62, a display screen (medical care document display screen 90) having the first display area 91 for displaying the medical care document and the second display area 92 for displaying original data which is medical care data of an extraction source of the extracted data.

The operation method of the medical care support system 10 according to the first embodiment or the like comprises: the medical care document generation step of generating, by the medical care document generation unit 63, a medical care document (discharge summary 70) in which extracted data extracted from medical care data related to medical care of a patient is laid out in a predetermined format; and the display screen generation step of generating, by the display screen generation unit 62, a display screen (medical care document display screen 90) having the first display area 91 for displaying the medical care document and the second display area 92 for displaying original data which is medical care data of an extraction source of the extracted data.

In the first embodiment or the like, hardware structures of the processing units that execute various processes such as the GUI control unit 41, the request issuing unit 42, the request reception unit 61, the display screen generation unit 62, the medical care document generation unit 63, and the change content learning unit 100 are various processors as shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a circuit configuration designed exclusively for executing various types of processing, and the like.

One processing unit may be configured by one of various processors, or may be configured by a combination of two or more processors of the same or different kinds (for example, a combination of a plurality of FPGAs or a combination of a CPU and an FPGA). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as hardware structures.

More specifically, the hardware structure of these various processors is an electrical circuit (circuitry) in the form of a combination of circuit elements, such as semiconductor elements.

EXPLANATION OF REFERENCES

10: medical care support system
11: client terminal
12: medical care support device
13: server group
14: network
21: electronic medical record server
21A: medical record database
22: image server
22A: image database
23: report server
23A: report database
31: CPU
32: memory
33: storage
34: communication unit
35: connection circuit
36: display unit
37: operation unit
39: operation program
41: GUI control unit
42: request issuing unit
51: CPU
52: memory
53: storage
54: communication unit
55: connection circuit
59: operation program
61: request reception unit
62: display screen generation unit (change unit)
63: medical care document generation unit
70: discharge summary (medical care document)
71: patient basic information display field
72: user information display field
73: hospitalization information display field
74: referral information display field
75: patient profile display field
80: medical record information display field
81: examination/treatment content display field
81A, 81B: examination field
81C: surgery field
81D: finding field
81E: prescription field
90: medical care document display screen
91: first display area
92: second display area
93: third display area
95: cursor
96, 97, 98: frame
99: scroll bar
100: change content learning unit
A1: doctor
A2: doctor
B1: doctor
N1: technician
G1, G2, G19: group

What is claimed is:

1. A medical care support device comprising
a processor configured to:
  determine a predetermined format for a layout of a medical care document;
  extract data from medical care data related to medical care of a patient;
  generate the medical care document in which the extracted data of the patient is laid out in the predetermined format;
  generate a display window having a first display area for displaying the medical care document, a second display area for displaying original data, and a third display area for displaying a plurality of medical time periods in time series, wherein the original data is the medical care data of an extraction source of the extracted data, and wherein the plurality of medical time periods are periods in which the medical care related to an acquisition of each piece of the medical care data is performed;
  display the extracted data in the medical care document and the extracted data in the original data in an identifiable manner on the display window, wherein the identifiable manner is a visual effect highlighting the extracted data in the medical care document and the extracted data in the original data; and
  highlight, in a case where any of the extracted data is selected in the first display area, the medical care period corresponding to the selected extracted data in the third display area.

2. The medical care support device according to claim 1, wherein the processor is configured to highlight, in a case where any of the extracted data is selected in the first display area, the original data corresponding to the selected extracted data in the second display area.

3. The medical care support device according to claim 1, wherein the processor is configured to display the extracted data and the medical care period in another identifiable manner on the display window.

4. The medical care support device according to claim 1, wherein the processor is configured to display the original data and the medical care period in another identifiable manner on the display window.

5. The medical care support device according to claim 1, wherein the processor is configured to highlight, in a case where any of the medical care period is selected in the third display area, the original data corresponding to the selected medical care period in the second display area.

6. The medical care support device according to claim 1, wherein the processor is configured to:
receive a change request to change the extracted data constituting the medical care document; and
change the extracted data according to the received change request.

7. The medical care support device according to claim 1, wherein the processor is configured to:
select the extracted data displayed in the first display area, as unchanged data; and
change, by selecting the medical care period displayed in the third display area, the unchanged data constituting the medical care document to the medical care data acquired at the selected medical care period.

8. The medical care support device according to claim 6, wherein the processor is configured to reflect a content of the change in a generation algorithm used to generate the medical care document.

9. The medical care support device according to claim 1, wherein the processor is configured to generate the medical care document by using a generation algorithm corresponding to a type of the medical care document generated from the generation algorithm constructed for each type of the medical care document.

10. The medical care support device according to claim 1, wherein when the predetermined format is in a first layout, the extracted data comprises first data,
wherein when the predetermined format is in a second layout different from the first layout, the extracted data comprises second data different from the first data.

11. The medical care support device according to claim 1, wherein a data amount of the original data is larger than a data amount of the extracted data.

12. The medical support device according to claim 1, wherein the processor is configured to:
display the extracted data in the medical care document on the display window with a first visual effect on the display window, and
in response to the extracted data in the medical care document being selected, display the extracted data in the original data with the first visual effect on the display window.

13. A non-transitory computer readable recording medium storing a medical care support program, the medical care support program causing a computer to execute:
determining a predetermined format for a layout of a medical care document;
extracting data from medical care data related to medical care of a patient;
generating the medical care document in which the extracted data of the patient is laid out in the predetermined format;
generating a display window having a first display area for displaying the medical care document, a second display area for displaying original data, and a third display area for displaying a plurality of medical time periods in time series, wherein the original data is the medical care data of an extraction source of the extracted data, and wherein the plurality of medical time periods are periods in which the medical care related to an acquisition of each piece of the medical care data is performed;
displaying the extracted data in the medical care document and the extracted data in the original data in an identifiable manner on the display window, wherein the identifiable manner is a visual effect highlighting the extracted data in the medical care document and the extracted data in the original data; and
highlighting, in a case where any of the extracted data is selected in the first display area, the medical care period corresponding to the selected extracted data in the third display area.

14. A medical care support method comprising:
executing, on a computer, the medical care support program stored in the non-transitory computer readable recording medium according to claim 13.

15. A medical care support device comprising
a processor configured to:
determine a predetermined format for a layout of a medical care document;
extract data from medical care data related to medical care of a patient;
generate the medical care document in which the extracted data of the patient is laid out in the predetermined format;
generate a display window having a first display area for displaying the medical care document, a second display area for displaying original data, and a third display area for displaying a plurality of medical time periods in time series, wherein the original data is the medical care data of an extraction source of the extracted data, and wherein the plurality of medical time periods are periods in which the medical care related to an acquisition of each piece of the medical care data is performed; and
in response to a first piece of the extracted data in the medical care document being selected, display the first piece of the extracted data in the medical care document, the first piece of the extracted data in the original data, and a first medical care period, among the plurality of medical care periods in the time series, in which the medical care related to the first piece of the extracted data is performed in an identifiable manner on the display window.

16. A non-transitory computer readable recording medium storing a medical care support program, the medical care support program causing a computer to execute:
determining a predetermined format for a layout of a medical care document;
extracting data from medical care data related to medical care of a patient;
generating the medical care document in which the extracted data of the patient is laid out in the predetermined format;
generating a display window having a first display area for displaying the medical care document, a second display area for displaying original data, and a third display area for displaying a plurality of medical time periods in time series, wherein the original data is the medical care data of an extraction source of the extracted data, and wherein the plurality of medical time periods are periods in which the medical care related to an acquisition of each piece of the medical care data is performed; and
in response to a first piece of the extracted data in the medical care document being selected, displaying the first piece of the extracted data in the medical care document, the first piece of the extracted data in the original data, and a first medical care period, among the plurality of medical care periods in the time series, in which the medical care related to the first piece of the extracted data is performed in an identifiable manner on the display window.

17. A medical care support method comprising:
executing, on a computer, the medical care support program stored in the non-transitory computer readable recording medium according to claim 16.

* * * * *